United States Patent [19]

Soufiane et al.

[11] Patent Number: 5,868,734
[45] Date of Patent: Feb. 9, 1999

[54] METHODS OF USING SILICA-TITANIA CLAD FIBERS

[75] Inventors: Abdelouahed Soufiane, Ames; Gerald J. Shirk, Cedar Rapids, both of Iowa

[73] Assignee: Iowa State University Research Foundation, Inc., Ames, Iowa

[21] Appl. No.: 564,509

[22] Filed: Nov. 29, 1995

[51] Int. Cl.⁶ ..................................................... A61N 5/06
[52] U.S. Cl. ............................ 606/15; 128/898; 606/16
[58] Field of Search ..................... 606/14–17; 385/141, 385/142, 144; 65/385; 128/898

[56] References Cited

U.S. PATENT DOCUMENTS

| | | |
|---|---|---|
| 2,326,059 | 8/1943 | Nordberg . |
| 3,958,058 | 5/1976 | Elmer . |
| 4,122,853 | 10/1978 | Smith . |
| 4,126,136 | 11/1978 | Auth et al. . |
| 4,170,997 | 10/1979 | Pinnow et al. . |
| 4,183,621 | 1/1980 | Kao et al. . |
| 4,184,860 | 1/1980 | Schneider . |
| 4,209,229 | 6/1980 | Rittler . |
| 4,273,109 | 6/1981 | Enderby . |
| 4,367,013 | 1/1983 | Guerder et al. . |
| 4,398,790 | 8/1983 | Righini et al. . |
| 4,592,353 | 6/1986 | Daikuzono . |
| 4,662,368 | 5/1987 | Hussein et al. . |
| 4,693,244 | 9/1987 | Daikuzono . |
| 4,702,759 | 10/1987 | Roba . |
| 4,729,373 | 3/1988 | Peyman . |
| 4,736,743 | 4/1988 | Daikuzono . |
| 4,832,979 | 5/1989 | Hoshino .................................. 427/38 |
| 4,867,776 | 9/1989 | Sharp . |
| 4,883,337 | 11/1989 | Dahlgren . |
| 4,932,989 | 6/1990 | Presby . |
| 5,037,174 | 8/1991 | Thompson . |
| 5,067,975 | 11/1991 | Backer et al. . |
| 5,100,507 | 3/1992 | Cholewa et al. . |
| 5,119,461 | 6/1992 | Beyer et al. . |
| 5,154,744 | 10/1992 | Blackwell et al. . |

(List continued on next page.)

FOREIGN PATENT DOCUMENTS

| | | |
|---|---|---|
| 1967211 | 9/1969 | Germany . |
| 60-42716 | 3/1985 | Japan . |
| 63-103843 | 5/1988 | Japan . |
| 63-313103 | 12/1988 | Japan . |
| 2244650 | 12/1991 | United Kingdom . |

OTHER PUBLICATIONS

Anter Laboratories, Inc., Graph entitled "Linear Thermal Expansion of Selected Materials" (1988).

J. Aoki et al., "Experimental Study and Clinical Application of New Ceramic Endoprobe with Nd–YAG Laser; Endoscopic Hemostatis, Pyloroplasty and Cutting Biopsy", *Lasers in Medicine*, 712, 2–8 (1986).

S. Ahsley et al., "Thermal Characteristics of Sapphire Contact Probe Delivery Systems for Laser Angioplasty", *Lasers in Surgery and Medicine*, 10, 234–244 (1990).

M.W. Berns et al., "Laser Applications in Biomedicine", *J. Laser Applications*, 34–39 (Fall 1988).

H.P. Berlien et al., "Laser in Medicine" in *Advances in Laser Medicine I, First German Symposium on Laser Angioplasty;* G. Biamino et al., Eds.; pp. 45–55 (1987).

J. Brumsted et al., "A Second Puncture Probe for Laparoscopic Delivery of the Nd:YAG Laser", *Obstetrics & Gynecology*, 73, 672–674 (Apr. 1989).

J.R. Brumsted et al., "Expanding GYN Applications of the Nd:YAG Laser", *Contemporary OB/GYN*, 34, 31–48 (Oct. 15, 1989).

Corning Incorporated Brochure entitled "ULE™ Titanium silicate Code 7971", Dec. 1990.

(List continued on next page.)

*Primary Examiner*—Michael Peffley
*Attorney, Agent, or Firm*—Mueting, Raasch & Gebhardt, P.A.

[57] ABSTRACT

Methods of delivering laser energy for medical procedures or industrial processes using an optical fiber having a core formed of a highly transmissive silica-based glass core and an outermost cladding layer of silica-titania glass.

19 Claims, 2 Drawing Sheets

U.S. PATENT DOCUMENTS

| | | | |
|---|---|---|---|
| 5,188,652 | 2/1993 | Nakamura et al. | |
| 5,196,005 | 3/1993 | Doiron et al. | 606/7 |
| 5,207,669 | 5/1993 | Baker et al. | 606/7 |
| 5,212,762 | 5/1993 | Shimada et al. | |
| 5,282,798 | 2/1994 | Bruse et al. | 606/17 |
| 5,348,552 | 9/1994 | Nakajima et al. | |
| 5,431,647 | 7/1995 | Purcell, Jr. et al. | 606/16 |
| 5,491,767 | 2/1996 | McPherson et al. | 606/16 X |
| 5,527,308 | 6/1996 | Anderson et al. | 606/14 |
| 5,536,265 | 7/1996 | van den Bergh et al. | 606/16 X |
| 5,755,850 | 5/1998 | Martin et al. | 606/16 |

OTHER PUBLICATIONS

N. Daikuzono, "Computer Controlled Contact Nd:YAG Laser System for Interstitial Local Hyperthermia", *Lasers in Medicine,* 712, 34 (1986).

R.C. DeVries et al., "The System $TiO_2$–$SiO_2$" *Trans. Brit. Ceram. Soc.,* 53, 525–540 (1954).

R. Dorn et al., "Perform Technologies for Optical Fibers", *Electrical Communications,* 62, 235–241 (1988).

S. Hessel et al., "Possibilities for the Use of Nd:YAG Laser in Vascular Recanalization", *Advances in Laser Medicine I, First German Symposium on Laser Angioplasty,* 89–95 (1986).

H. Ito et al., "Single–model optical fibers", *Chem. Abs.,* 109, Abstract No. 114984y (Oct. 3, 1988).

T. Izawa et al., "Fabrication Process of High Silica Fibers" in *Optical Fibers: Materials and Fabrication;* KIK Scientific: Tokyo; pp. 54–57, 64–69.

S.N. Joffe, "Contact Neodymium: YAG Laser Surgery in Gastroenterology: A Preliminary Report", *Lasers in Surgery and Medicine,* 6, 155–157 (1986).

K. Kamiya et al., "$TiO_2$–$SiO_2$ glasses prepared from metal alkoxides", *J. Mater. Sci.,* 15, 2937–2939 (1980).

R.Th. Kersten et al., "Laser Beam Delivery System for Medical Applications" in *Optical Fibers in Medicine;* A. Katzir, Ed.; SPIE Optical Engineering Press: Bellingham, Washington; pp. 395–398 (Jan. 1990).

J. Lammer et al., "Experimental and Clinical Results with Neodymium: YAG Laser Angioplasty", *Advances in Laser Medicine I, First German Symposium on Laser Angioplasty,* 96 (1986).

W.T. Minehan et al., "Titania–Silica Glasses Prepared by Sintering Alkoxide Derived Spherical Colloids", *J. Non–Crystalline Solids,* 108, 163–168 (Mar. 1989).

M. Moretti, "A Status Report on Lasers in Medicine", *Laser Focus/Electro–Optics,* 82–97 (Apr. 1987).

P.C. Schultz, "Binary titania–Silica Glasses Containing 10 to 20 Wt% $TiO_2$", *J. Am. Ceramic Society,* 59, 214–219 (Jun. 1976).

P.C. Schultz et al., "Ultra–Low–Expansion Glasses and Their Structure" in *Glasses and the Vitreous State;* J. Zarzycki, Ed.; Cambridge University Press: Cambridge; pp. 454–461 (1991).

R.S. Scott, "Surgical Applications of the Sapphire Contact Probe and the Nd:YAG Laser", *Optical and Laser Technology in Medicine,* 605 (Jan. 1986).

G. Shirk et al., "Contact Surgery with Sculptured Quartz Fibers Using an Nd:YAG, Argon, or KTP Laser: Alteration of Lateral Thermal Damage Effects by Variation of Fiber Tip Geometry at Low Laser Power Output".

G. Shirk et al., "Contact Surgery with Sculptured Quartz Fibers Using an Nd:YAG, Argon, or KTP Laser: Thermal Damage Effects Caused by Power Variation".

G.J. Shirk, "Use of the Nd:YAG Laser for the Treatment of Endometriosis", *Am. J. Obstetrics and Gynecology,* 160, 1344–1351 (Jun. 1989).

G. Shirk et al., "Operative Laparoscopy with the Nd:YAG Laser in the Treatment of Endometriosis and Pelvic Adhesions" *Lasers in Surgery and Medicine,* 11, 297–300 (1991).

G.J. Shirk et al., "Comparison of Tissue Effects with Sculptured Fiberoptic Cables and Other Nd:YAG Laser and Argon Laser Treatments", *Lasers in Surgery and Medicine,* 11, 563–568 (1991).

B.J. Skutnik et al., "High Strength, Hard–Coated All Silica Optical Fiber for Laser Surgery", *Optical Fibers in Medicine IV,* 1067, 211–218 (1989).

S. Suzuki et al., "Experimental Studies of Endoscopic Local Hyperthermia with Contact Nd:YAG Laser", *Lasers in Medicine,* 712, 15–21 (1986).

5,868,734

METHODS OF USING SILICA-TITANIA CLAD FIBERS

FIELD OF THE INVENTION

The present invention relates to the field of optical fibers useful for transmitting laser energy. More particularly, the present invention relates to methods of delivering laser energy in medical procedures or industrial processes, where the optical fibers are constructed of a core clad with an outermost layer of silica-titania glass.

BACKGROUND OF THE INVENTION

The use of energy delivered by optical fibers in medical procedures and industrial processes is known. The desired effects caused by the energy can be thermal, photodisruptive or photo-chemical.

In many medical procedures, energy delivered by optical fibers is used for its thermal effect. That thermal effect is dependent upon the specific way the energy delivered by the optical fiber is transferred to thermal energy in the tissue. One laser used in medical procedures is the carbon dioxide ($CO_2$) laser whose wavelength at 10.6 $\mu$m makes it opaque to cellular water. The $CO_2$ laser is therefore totally absorbed by water and rapidly converted to thermal energy over a very short distance (<100 $\mu$m).

Recently, Nd:YAG laser systems, coupled to silica fibers with either sculptured or bare tips or with sculptured sapphire tips, have shown great benefits as surgical tools when used for certain procedures. Using these laser systems with a bare fiber, photocoagulation to tissue depths of 4 to 5 mm in tissue can be attained in a non-contact mode. In a contact mode, incision and cauterization of the nearby tissue can be achieved.

These two capabilities, though providing the surgeon with new and powerful tools in performing procedures that are very close to being hemostatic, have as yet to be integrated into a full spectrum of optical fiber surgical systems. At one extreme, only photocoagulation can be achieved in a non-contact mode while at the other extreme only incision can be achieved in a contact mode. Between these two extremes, there is a range of combined and controlled photocoagulation and incision that would be highly desirable, and a fiber optic system that could provide this full-spectrum capability would provide the surgeon with a broad range of new surgical capabilities to meet the specific needs of a broad range of surgical procedures.

The most common optical fiber material used for the delivery of energy at the present time is silica glass. Indeed, the same glass chemistry presently used in typical optical fibers for laser surgery is also used in telecommunication optical fibers. These optical fibers are capable of transmitting light energy through very small diameters and they can be threaded to almost any part of the body creating little or no damage to surrounding normal tissue. As a result, fiber optic delivery systems are useful in conjunction with endoscopic procedures and catheter-based delivery systems.

Common silica fibers can be highly effective in photocoagulating tissue in a non-contact mode. However, when common silica fibers come into contact with tissue or blood there is significant thermal-mechanical damage to the fiber and disruption of energy transmission. Because of the absorption of light energy at the tissue contact surface, the fiber tip is rapidly heated to high temperatures thereby destroying the tip. The effect on the surrounding tissue is variable and has an unpredictable tissue damage pattern.

The thermal-mechanical breakdown of the optical fiber that follows the use of the fiber in a contact mode also typically result in contamination of the incisional site with silica glass fragments in addition to preventing further photocoagulation due to absorption of energy by the degraded tip. These fragments may present a bio-hazard as their effect on tissue has not been fully studied. Perhaps more importantly, the use of a technique for precise laparoscopic dissection that creates a variable tissue effect with significant lateral coagulation is less than optimal.

Attempts have also been made to provide optical fibers which, for example, have sapphire contact tips or infrared absorbing materials at their tips to control the dispersion of energy from the tip and/or the thermal-mechanical breakdown. These attempts have not met with success because, even though they may be specifically designed for contact applications, all of the fibers suffer from the same thermal and/or chemical degradation described above for the silica fiber tips.

As a result, although known optical fibers can provide adequate performance when used in non-contact applications to accomplish photocoagulation or other photo-chemical effects, the reality facing surgeons is that contact between the fiber tips and tissue is extremely difficult to avoid due to the close quarters in which these devices operate. After the initial contact and degradation occurs, the performance of the fiber can no longer be accurately predicted. If predictable characteristics are required, a new fiber tip must be created, either by cutting and polishing a new tip or by replacing the entire fiber. Both of these options increase the cost of the procedure and increase the time need to complete it.

One approach to address these problems was developed by one of the inventors of the present application and described in U.S. patent application Ser. No. 08/209,002, filed on 10 Mar. 1994, which is hereby incorporated by reference, describes the use of an optical fiber having a core of silica glass doped with titanium dioxide. That particular material provides an extremely low coefficient of thermal expansion. As a result, optical fibers made with sufficient amounts of titania (typically 6–8%) do not suffer from the thermal expansion degradation effects described above for fibers constructed of other materials.

Those fibers are, however, difficult to produce in that the preforms should be pulled into fibers in an air or oxygen atmosphere to maintain the titanium in the doped preform in its highest ($Ti^{+4}$) oxidation state. If an air or oxygen atmosphere is not used, then the resulting fibers may contain significant amounts of reduced titanium ($Ti^{+3}$) which absorbs energy in the visible and near infrared regions. As a result, those fibers suffer from a loss in performance when used with the significant numbers of medical lasers operating in the visible/near infrared regions.

Another disadvantage of optical fibers with silica-titania cores is that, although they transmit significant amounts of energy, they are not as efficient as typical silica glass cored fibers. In general, silica-titania glass cored fibers transmit only about t 75– 80% of energy in part because the commercially available preforms are not designed for use in fiber optics. In contrast, the rate of transmission of typical silica glass cored fibers is at least about 95%.

Optical fiber systems currently used for medical procedures, silica or otherwise, remain useful as photocoagulating or incisional tools only so long as they are used in non-contact procedures. Given the close nature of the environments in which these devices operate, however, contact and the resulting degradation are difficult, if not impossible, to avoid. Furthermore, the use of silica-titania glass fibers addresses the thermal degradation problems, but suffers from other disadvantages.

In addition to the methods of medical treatment useful using optical fibers, many industrial processes relying on thermal effects produced by laser energy delivered by optical fibers for cutting, brazing, welding, soldering, ablation, marking and other industrial processes. Many of those processes expose the optical fiber tip to thermal energy that results in thermal/chemical degradation of the tip similar to that found in the medical procedures described above. In some instances it may be desirable to place the fiber tip in contact with the materials being processed, but that option may not be available because of the damage it would cause to the fiber tip. The problems of thermal degradation may, in fact, be more acute in industrial processes due to the typically higher energy levels associated with industrial lasers.

One attempt at preventing or controlling degradation of optical fiber tips in industrial processes including shrouding them to provide a positive pressure environment to prevent contact between the tips and the materials being heated. Such approaches, however, increase the cost and complexity of systems incorporating optical fiber delivery systems.

As a result, there is a need for an optical fiber that provides predictable operating characteristics in thermal either a contact or non-contact mode, can transmit significant amounts of energy, and can be manufactured using existing fiber technology.

SUMMARY OF THE INVENTION

Methods according to the present invention comprise transmitting laser energy using an optical fiber having a highly transmissive silica-based glass core and an outermost cladding of silica-titania glass. The processes in which the method has application include medical procedures and industrial processes in which the tip of the optical fiber is subjected to thermal energy sufficient to degrade typical silica glass optical fibers.

One advantage of methods according to the present invention is that the optical fiber used in the method provides optimal performance by using materials where their characteristics are most beneficial. By using a highly transmissive core material, the efficiency of the optical fiber is optimized. Likewise, by using silica-titania glass as the outermost cladding for the core, the optical fiber can provide the benefits associated with the low coefficient of thermal expansion of that material.

Another advantage of methods according to the present invention is that the optical fiber exhibits increased shock resistance, tensile strength, and bending strength as compared to typical optical fibers due to compressive stresses caused by the low coefficient of thermal expansion of the silica-titania glass used for the outermost cladding of the optical fiber. Furthermore, optical fibers used in methods according to the present invention also provide increased chemical resistance over typical optical fiber core and cladding materials.

With regard to medical procedures, the methods according to the present invention may involve purposeful tissue contact and in others, the procedures may involve no purposeful contact with tissue.

Another advantage of methods according to the present invention is that the same optical fiber can be used in contact or distanced from the materials (in industrial applications) or tissues (in medical procedures). As one medical example, the method can involve using the optical fiber for contact cauterization and/or incision, followed by non-contact use for incision, photocoagulation or other photo-chemical treatment without replacing the fiber or repairing its tip.

A further advantage of methods according to the present invention is that the performance of the optical fiber remains substantially constant after contact with tissue or other materials.

These and other features and advantages of the methods according to the present invention are described in the detailed description and claims presented below.

DETAILED DESCRIPTION OF THE INVENTION

Figure 1:
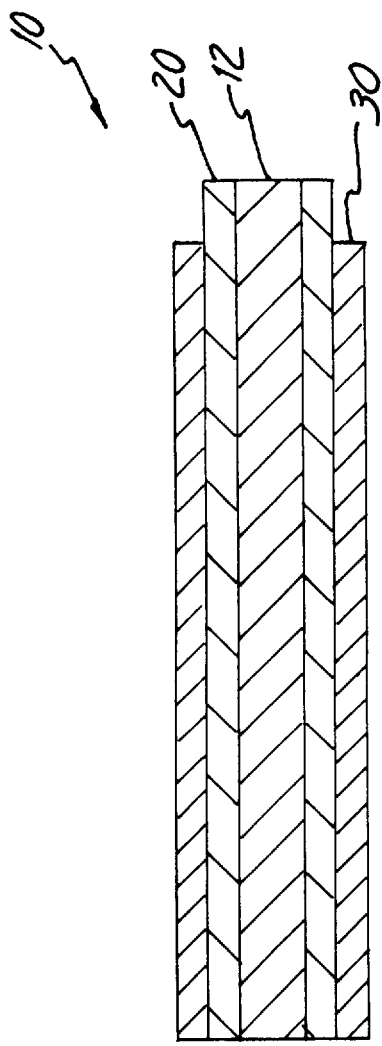
FIG. 1 is a schematic diagram in cross-section of one optical fiber useful in methods according to the present invention.

Methods according to the present invention involve delivering laser energy using optical fibers having highly transmissive silica-based glass cores having an outermost cladding of silica-titania glass. By cladding a transmissive core with silica-titania glass, the best properties of both materials can be exploited. The core material can be formed of materials having the desired transmissive properties (depending on the energy being transmitted) while the outermost cladding of the fiber can take advantage of the extremely low coefficient of thermal expansion of silica-titania glass.

The methods in which the present invention is useful include performing medical procedures as well as industrial processes.

Medical procedures in which silica-titania glass clad fibers are useful include any procedure in which fiber-tissue contact is expected or possible. As a result, the procedures could include non-contact treatments such as photocoagulation or incision and/or treatments involving planned fiber-tissue contact such as incision or photo-irradiation. In addition, fibers could be provided for medical procedures in which contact was to be avoided, but may occur due to the tight quarters in which the procedure is performed in vivo.

Some medical procedures that are particularly advantageous when performed according to the present invention are those involving tissue photo-irradiation, i.e., the heating of tissue to thermal destruction by inserting an optical fiber into a tissue mass and transmitting energy through the fiber to heat the tissue to destruction. As described above, such a procedure would result in destruction of the fiber itself if performed using conventional optical fibers. Examples of such procedures include, but are not limited to: coagulation of uterine fibroids, treatment of benign prostatic hypertrophy, treatment of malignant tumor masses to reduce tumor volume, and coagulation of vascular abnormalities.

Among the benefits of photo-irradiation is that the efficiency of the process would be limited only by the rate of energy transmission of the fiber itself. There would be no concern for the effects of energy dispersion and absorption by surrounding materials/tissues that are characteristic of procedures in which the energy exits the fiber and travels some distance before striking the intended tissue.

Methods according to the present invention could be used with laser energy from the near infrared range through the ultraviolet wavelengths, depending on the desired effect and the exact composition of the core materials used in the optical fibers.

As discussed herein, the cores of optical fibers useful in connection with methods according to the present invention are constructed of silica-based glasses that are highly transmissive. In one preferred method, the provided optical fiber core transmits about 90% or more of energy from the proximal end to the distal end. In a more preferred method, the provided optical fiber core transmits 95% or more of energy from the proximal end to the distal end.

FIG. 1 is a cross-sectional schematic diagram of one fiber useful in methods according to the present invention. Fiber 10 includes a core 12 comprising a highly transmissive silica-based glass. Cladding core 12 is a layer 20 of silica-titania glass while a jacket 30 of a suitable polymer or other protective material completes the construction of fiber 10.

As with any optical fiber, it is advantageous to provide a core 12 of material having a higher index of refraction than the index of refraction of the silica-titania glass cladding 20 to provide for total-internal-reflection (TIR) along the fiber 10.

The preferred silica-titania glass cladding comprises about 92–94 wt % $SiO_2$ and the balance (6–8 wt %) in $TiO_2$. The most preferred silica-titania glass cladding comprises 92.5% $SiO_2$ and 7.5% $TiO_2$ and has an index of refraction of about 1.4828. Because pure silica glass has an index of refraction of about 1.4584, it is advantageous to dope the silica glass core 12 to raise its index of refraction to equal or exceed the index of refraction of the silica-titania glass cladding to provide for TIR. One example of a suitable core material would be Germania-doped silica glass where the concentration of $GeO_2$ is greater than or equal to 30%.

Figure 2:
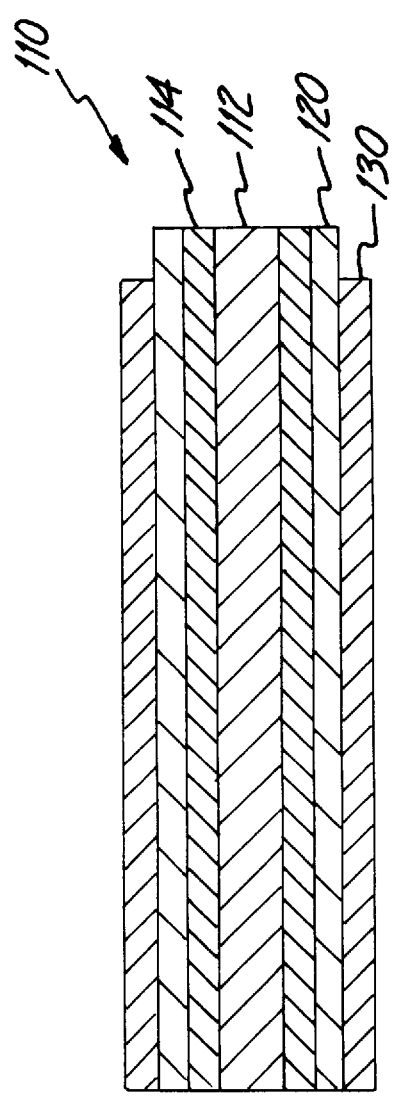
FIG. 2 is a schematic diagram in cross-section of another optical fiber useful in methods according to the present invention.

FIG. 2 is a cross-sectional schematic diagram of an alternate fiber construction useful in methods according to the present invention. Fiber 110 includes a core 112 comprising a silica-based glass having a relatively high rate of energy transmission. Core 112 is clad with a layer 114 of another silica-based glass (not silica-titania) that has a lower refractive index that the glass making up core 112. An overcladding layer of silica-titania glass 120 is then located over the cladding glass 114 while an outer jacket 130 of a suitable polymer or other protective material completes the construction of fiber 110.

By providing the cladding layer 114, the optical properties of the core 112 can be optimized without sacrificing the TIR necessary to propagate light for long distance along the fiber 110. Table 1 below lists some alternatives for the core 112 and cladding 114 that may be helpful for optical fibers used in methods according to the present invention.

TABLE 1

| Core Material | Cladding Material |
| --- | --- |
| $SiO_2$ | $F—SiO_2$ |
| | $F—P_2O_5—SiO_2$ |
| $SiO_2—GeO_2$ | $SiO_2$ |
| | $SiO_2—P_2O_5$ |
| | $F—SiO_2$ |
| | $F—P_2O_5—SiO_2$ |

TABLE 1-continued

| Core Material | Cladding Material |
| --- | --- |
| $SiO_2—GeO_2—B_2O_3$ | $SiO_2—P_2O_5—B_2O_3$ |
| $SiO_2—GeO_2—P_2O_5$ | $SiO_2—P_2O_5—B_2O_3$ |
| | $F—P_2O_5—SiO_2$ |
| $SiO_2—TiO_2$ | $SiO_2$ |
| | $SiO_2—P_2O_5$ |
| | $F—SiO_2$ |
| | $F—P_2O_5—SiO_2$ |

The various combinations provided for the core 112 and cladding 114 are only examples. Other combinations of silica-based glass cores 112 and cladding materials could be substituted for those listed above, provided they meet the requirements of transmissive core clad with a glass having a lower index of refraction than the core 112.

Furthermore, for those combinations including a core 112 of $SiO_2—TiO_2$, it should be understood that weight % of titania is low as compared to the composition of the outer cladding layer 120 of silica-titania glass. Typically, the weight % of titania in the core 112 would only be sufficient to raise the index of refraction of the core 112 without significantly affecting the ability of the core 112 to transmit laser energy. In one preferred method, the amount of titania in the core 112 would not exceed about 2–3 weight %. Even more preferably, the weight % of titania would not exceed about 1%.

In some instances, it may also be desirable to avoid the introduction of any titania into the core.

One preferred composition of a fiber 110 includes a pure silica glass core 112 (with an index of refraction of 1.4584) clad with a layer 114 of fluorine-doped silica glass (4 wt %) to lower its index of refraction to about 1.4414. As with the fiber 110, the most preferred composition for the overcladding of silica-titania glass is 92.5% $SiO_2$ and 7.5% $TiO_2$.

In this fiber the core 112 has a diameter of about 600 μm, the fluorine-doped silica glass cladding 114 has a thickness of about 50–100 μm, and the outer layer 120 of silica-titania glass has a thickness of about 150 μm. It is preferred that the outer layer 120 of silica glass be provided thicker than is typically necessary in cladding layers provided for optical considerations. By providing a thicker outer layer of silica-titania glass the thermal expansion and chemical resistance benefits are most advantageously exploited. As applied to optical fibers used in methods according to the present invention, it may be preferred to provide a core-to-cladding ratio of about 4:1. It may be more preferred to decrease that ratio to about 3:1 or less for more severe applications.

The fiber described in the above paragraph also provides a graded change in the coefficients of thermal expansion moving from the core 112 to the overcladding layer 120. The coefficient of thermal expansion of the core material is about $5.5 \times 10^{-7}$, while the fluorine-doped cladding layer has a coefficient of thermal expansion of about $2.5 \times 10^{-7}$. The overcladding layer, however, has a coefficient of thermal expansion of about $0.5 \times 10^{-7}$.

All of the optical fibers described above can be manufactured using known methods and processes. Some of those processes involve vapor deposition and include chemical vapor deposition (CVD), modified chemical vapor deposition (MCVD), and outside vapor phase oxidation (OVPO). Another process that may be useful is typically referred to as sol-gel.

Other methods of providing optical fibers for use in methods according to the present invention involve the use of "rod-in tube" processing. In this method, a silica based preform is mounted in the feed system of a fiber pulling machine along with a prepolished tube of the desired silica-titania glass to be used for the outermost cladding of the fiber. As the preform and silica-titania tube are pulled into a fiber, the tube of silica-titania glass collapses onto the surface of the silica-based preform.

Figure 3:
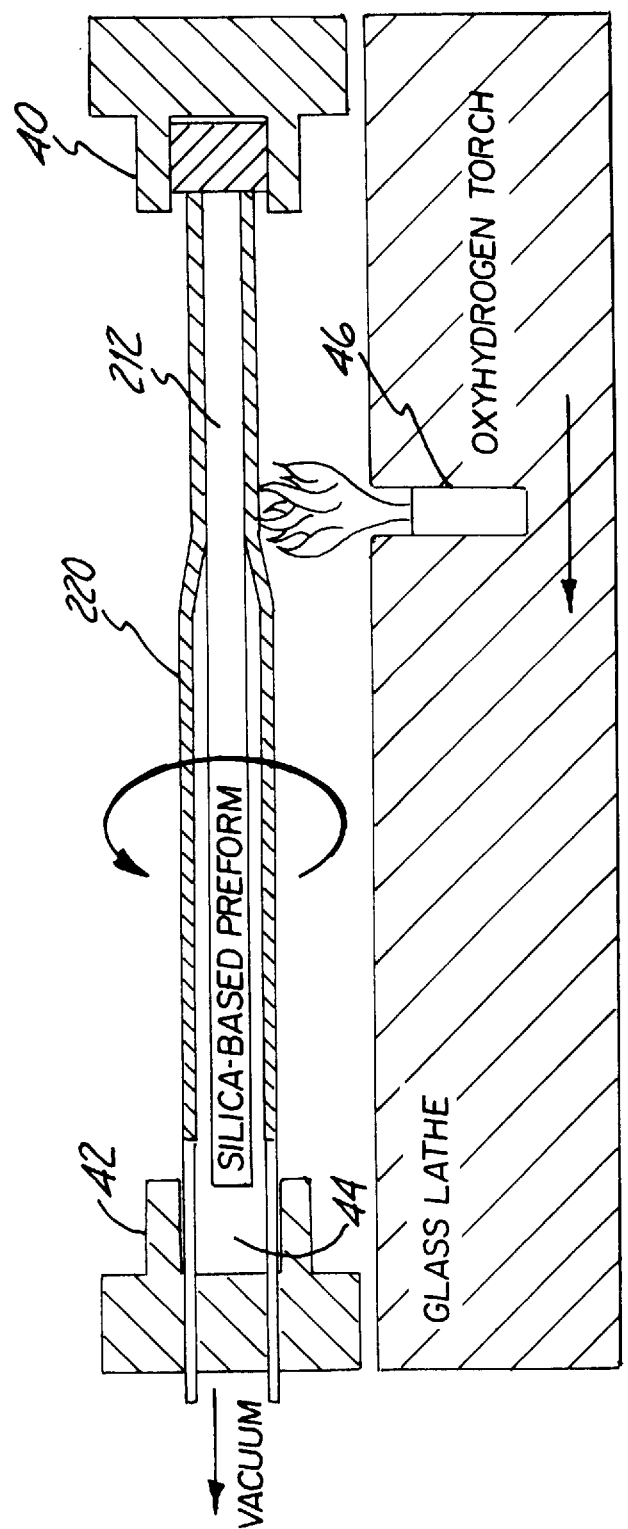
FIG. 3 is a schematic diagram of one process useful to provide preforms for pulling optical fibers useful in methods according to the present invention.

Another method for providing optical fibers useful for methods according to the present invention is an overcollapsing method in which a tube of silica-titania glass is collapsed over a silica-based preform that may include cladding as described above with respect to fiber 110. FIG. 3 schematically depicts an overcollapsing process.

The preform 212 is loaded into a glass lathe having two chucks 40 and 42. The tube of silica-titania glass 220 is loaded over the preform 212. A vacuum is then drawn from one end to provide a vacuum between the preform and silica-titania glass tube. Both the preform 212 and silica-titania glass tube 220 are then rotated while a thermal source 46, such as an oxyhydrogen torch is moved axially between the chucks 40 and 42 to soften and collapse the tube 220 of silica-titania glass onto the surface of the preform 212. The vacuum aids in collapsing the tube 220 as well as reducing bubbles between the silica-titania glass and the preform.

After the silica-titania glass tube 220 is completely collapsed onto the preform 212, they are loaded into a fiber-drawing machine where an optical fiber can be pulled from the composite.

Although it may be helpful to perform such collapsing process and fiber pulling in an oxygen atmosphere to maintain the titanium in the tube 220 in its highest ($Ti^{+4}$) oxidation state, it is not necessary because in most formulations of fibers useful in methods according to the present invention, the core material of the resulting optical fiber will not contain titania. Although the outermost cladding of the fibers, which do contain titania, may experience a reduction of the titania from $Ti^{+4} \rightarrow Ti^{+3}$, that will not significantly affect the fibers' rates of transmission because the transmission is conducted along the cores of the fibers, not the outer cladding.

Optical fibers produced using the principles of the invention are preferably jacketed with a hard protective plastic material such as Teflon, Tefzel, polyimide-buffer, Nylon, UV-curable multifunctional acrylate or a combination of these or similar materials. One preferred jacketing material is a hard fluoroacrylate material, although other materials can also be used, including, but not limited to silicone acrylate polymers and other materials. The most preferred material is a hard, UV-curable multifunctional fluoroacrylate material that is highly fluorinated to increase its strength. The material is sold by DSM Desotech Inc., Elgin, Illinois under the tradename DESOLITE (Product Code 3471C2-79).

Another advantage of methods according to the present invention is that the silica-titania glass cladding provides increased chemical-resistant properties as opposed to other silica glasses. In particular, the silica-titania glass resists hydration which can degrade transmission of energy through the fiber. In addition, silica-titania glass is also acid-resistant and may provide a surface with higher-release properties than common silica glass, i.e., materials or tissue do not adhere as strongly to silica-titania glass as they might to other silica glasses.

Tables 2–7 below are the actual results of tests conducted using an optical fiber with a pure silica glass core clad with a layer of fluorine-doped silica glass (4 wt %) and overclad with silica-titania glass (92.5% $SiO_2$/7.5% $TiO_2$) as compared to a commercial medical-grade silica fiber (polymer jacketed fused silica glass).

The tests involved ambient temperature chicken breast tissue into which the silica-titania clad fibers were inserted during transmission of laser energy produced using a Nd:YAG 1064 nm laser operating at 10 or 20 Watts or scanned over the surface of the tissue using a Nd:YAG 1064 nm laser operating at 20 or 30 Watts. In contrast, the commercial fibers were only scanned over the surface of the tissue (in contact with the tissue, but not inserted below the surface). The commercial fibers were not inserted into the tissue because the degradation would have been too rapid to easily measure.

The results of the tests show the improved performance of optical fibers used in methods according to the present invention.

TABLE 2

Silica-Titania Clad Fiber with Power Level of 10 Watts Inserted in Tissue

| Lasing Time (sec) | Transmission After Lasing (Watts) | Percent Transmission Loss |
| --- | --- | --- |
| 30 | 10 | 0 |
| 60 | 10 | 0 |
| 120 | 10 | 0 |
| 240 | 10 | 0 |

TABLE 3

Commercial Fiber with Power Level of 10 Watts Scanned Over Tissue

| Lasing Time (sec) | Transmission After Lasing (Watts) | Percent Transmission Loss |
| --- | --- | --- |
| 30 | 9.84 | 1.6 |
| 60 | 9.76 | 2.4 |
| 120 | 9.64 | 3.6 |
| 240 | 9.60 | 4 |

TABLE 4

Silica-Titania Clad Fiber with Power Level of 20 Watts Inserted in Tissue

| Lasing Time (sec) | Transmission After Lasing (Watts) | Percent Transmission Loss |
| --- | --- | --- |
| 30 | 20 | 0 |
| 60 | 19 | 5 |
| 120 | 14 | 30 |
| 240 | 13 | 35 |

TABLE 5

Commercial Fiber with Power Level of 20 Watts Scanned Over Tissue

| Lasing Time (sec) | Transmission After Lasing (Watts) | Percent Transmission Loss |
| --- | --- | --- |
| 30 | 18.5 | 8 |
| 60 | 17.6 | 12 |
| 120 | 17.4 | 13 |
| 240 | 10.5 | 48 |

TABLE 6

Silica-Titania Clad Fiber with Power Level of 20 Watts Scanned Over Tissue

| Lasing Time (sec) | Transmission After Lasing (Watts) | Percent Transmission Loss |
|---|---|---|
| 240 | 20 | 0 |

TABLE 7

Silica-Titania Clad Fiber with Power Level of 30 Watts Scanned Over Tissue

| Lasing Time (sec) | Transmission After Lasing (Watts) | Percent Transmission Loss |
|---|---|---|
| 240 | 30 | 0 |

Having thus described some preferred methods according to the present invention, it will be evident to those skilled in the art that various changes and modifications can be made without departing from the scope of the invention as described by the claims appended hereto.

What is claimed is:

1. A method of performing an in vivo medical procedure comprising:
   a) providing an optical fiber having proximal and distal ends, the optical fiber comprising:
      1) a highly transmissive core comprising silica-based glass;
      2) an outermost cladding layer located on the core, the outermost cladding layer comprising silica-titania glass that is less transmissive than the silica-based glass core, wherein the ratio of the diameter of the core to the thickness of the outermost cladding is about 4:1 or less;
   b) introducing the distal end of the optical fiber into the body of a patient;
   c) transmitting energy from the proximal end of the optical fiber through the distal end of the optical fiber to perform a medical procedure.

2. A method according to claim 1, wherein the step of providing an optical fiber further comprises providing an optical fiber having a core that transmits about 90% or more of laser energy from the proximal to the distal end of the optical fiber.

3. A method according to claim 1, wherein the step of providing an optical fiber further comprises providing an optical fiber having a core that transmits about 95% or more of laser energy from the proximal to the distal end of the optical fiber.

4. A method according to claim 1, wherein the step of providing an optical fiber further comprises providing an optical fiber having an outermost cladding layer comprising 6–8 wt % titania.

5. A method according to claim 1, wherein the step of providing an optical fiber further comprises providing an optical fiber having an outermost cladding layer consisting essentially of 92.5 wt % silica glass and 7.5 wt % titania.

6. A method according to claim 1, wherein the step of providing an optical fiber further comprises providing an optical fiber having a cladding layer located between the core and the outermost cladding, the cladding layer comprising a material having an index of refraction less than the index of refraction of the silica-based glass forming the core.

7. A method according to claim 6, wherein the material of the cladding layer has a coefficient of thermal expansion less than the coefficient of thermal expansion of the silica-based glass forming the core and greater than the coefficient of thermal expansion of the silica-titania glass forming the outer cladding of the optical fiber.

8. A method according to claim 1, wherein the step of introducing the distal end of the optical fiber into the body of a patient further comprises contacting tissue in vivo with the distal end of the optical fiber.

9. A method according to claim 8, further comprising a step of removing the distal end of the optical fiber from contact with the tissue after the step of transmitting energy to perform a medical procedure, and still further comprising a step of transmitting energy from the proximal end through the distal end of the optical fiber, the energy exiting the distal end of the fiber and impinging on tissue in vivo to perform further medical procedures, wherein substantially all of the energy exits from the distal end of the optical fiber.

10. A method of performing an in vivo medical procedure comprising:
    a) providing an optical fiber having proximal and distal ends, the optical fiber comprising:
       1) a core comprising silica-based glass that transmits about 95% or more of laser energy from the proximal to the distal end of the optical fiber;
       2) an outermost cladding layer located on the core, the outermost cladding layer consisting essentially of 92.5 wt % silica glass and 7.5 wt % titania;
       3) a cladding layer located between the core and the outermost cladding, the cladding layer comprising a material having an index of refraction less than the index of refraction of the silica-based glass forming the core;
    b) introducing the distal end of the optical fiber into the body of a patient, wherein the distal end of the optical fiber contacts body tissue;
    c) transmitting energy from the proximal end of the optical fiber through the distal end of the optical fiber to perform a medical procedure, wherein the optical performance of the optical fiber remains substantially constant after contact with the body tissue.

11. A method according to claim 10, wherein the ratio of the diameter of the core to the thickness of the outermost cladding is about 4:1 or less.

12. A method according to claim 10, further comprising the steps of:
    a) removing the distal end of the optical fiber from contact with the tissue after the step of transmitting energy to perform a medical procedure; and
    b) transmitting energy from the proximal end through the distal end of the optical fiber after the step of removing the distal end of the optical fiber from contact with the tissue, the energy exiting the distal end of the fiber and impinging on tissue in vivo to perform further medical procedures, wherein substantially all of the energy exits from the distal end of the optical fiber.

13. A method of delivering laser energy to material to cause a thermal effect, the method comprising the steps of:
    a) providing an optical fiber having proximal and distal ends, the optical fiber comprising:
       1) a highly transmissive core comprising silica-based glass;
       2) an outermost cladding layer located on the core, the outermost cladding layer comprising silica-titania glass that is less transmissive than the silica-based glass core, wherein the ratio of the diameter of the core to the thickness of the outermost cladding is about 4.1 or less;

b) placing the distal end of the optical fiber proximate material to be processed;

c) transmitting energy from the proximal end of the optical fiber through the distal end of the optical fiber, the transmitted energy sufficient to raise the temperature of the material to cause a thermal effect.

14. A method according to claim 13, wherein the step of providing an optical fiber further comprises providing an optical fiber having a core that transmits about 90% or more of laser energy from the proximal to the distal end of the optical fiber.

15. A method according to claim 13, wherein the step of providing an optical fiber further comprises providing an optical fiber having a core that transmits about 95% or more of laser energy from the proximal to the distal end of the optical fiber.

16. A method according to claim 13, wherein the step of providing an optical fiber further comprises providing an optical fiber having an outermost cladding layer comprising 6–8 wt % titania.

17. A method according to claim 13, wherein the step of providing an optical fiber further comprises providing an optical fiber having an outermost cladding layer consisting essentially of 92.5 wt % silica glass and 7.5 wt % titania.

18. A method according to claim 13, wherein the step of providing an optical fiber further comprises providing an optical fiber having a cladding layer located between the core and the outermost cladding, the cladding layer comprising a material having an index of refraction less than the index of refraction of the silica-based glass forming the core.

19. A method according to claim 18, wherein the material of the cladding layer has a coefficient of thermal expansion less than the coefficient of thermal expansion of the silica-based glass forming the core and greater than the coefficient of thermal expansion of the silica-titania glass forming the outermost cladding of the optical fiber.

* * * * *